United States Patent
Cooper et al.

(10) Patent No.: US 9,918,731 B2
(45) Date of Patent: Mar. 20, 2018

(54) REMOTELY ACTUATED SURGICAL GRIPPER WITH SEIZE RESISTANCE

(71) Applicant: Intuitive Surgical Operations, Inc., Sunnyvale, CA (US)

(72) Inventors: Thomas G. Cooper, Menlo Park, CA (US); Daniel Saraliev, Santa Cruz, CA (US); Mathew R. Williams, Walnut Creek, CA (US); William A. McDonald, III, Cambell, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 964 days.

(21) Appl. No.: 13/936,077

(22) Filed: Jul. 5, 2013

(65) Prior Publication Data
US 2014/0012290 A1  Jan. 9, 2014

Related U.S. Application Data

(60) Provisional application No. 61/668,983, filed on Jul. 6, 2012.

(51) Int. Cl.
*A61B 17/00* (2006.01)
*A61B 17/29* (2006.01)
(Continued)

(52) U.S. Cl.
CPC .......... *A61B 17/29* (2013.01); *A61B 17/3201* (2013.01); *A61B 34/30* (2016.02); *A61B 2017/2936* (2013.01); *A61B 2017/2939* (2013.01)

(58) Field of Classification Search
CPC ................ A61B 17/29; A61B 17/3201; A61B 2017/2936; A61B 2017/2939;
(Continued)

(56) References Cited

U.S. PATENT DOCUMENTS 3,780,416 A * 12/1973 Rider .................. A61B 17/128
29/243.56
4,146,412 A   3/1979 Schumacher et al.
(Continued)

FOREIGN PATENT DOCUMENTS

WO   WO-9610957 A1   4/1996
WO   WO-9915089 A1   4/1999

OTHER PUBLICATIONS

International Search Report and Written Opinion for Application No. PCT/US2013/49488, dated Oct. 8, 2013, 19 pages.
(Continued)

*Primary Examiner* — Christopher L Templeton
*Assistant Examiner* — Majid Jamialahmadi (57) ABSTRACT

A surgical end effector includes a clevis and one or more jaws pivotally coupled to the clevis. At least one jaw includes a slot. An axle assembly includes a bearing axle that rotatably supports a bearing, which may be a plain bearing. An actuator coupling is coupled to the bearing axle. The bearing engages the slot such that pushing and pulling on the actuator coupling causes one jaw to close against the other jaw. The bearing axle and the jaws may be made from materials that are prone to galling and the bearing may be made from a material that resists galling. The slot may include a lip that supports the bearings in a spaced apart relationship. The bearing axle may be less than 1.5 millimeters in diameter and each bearing may be less than 3.0 millimeters in diameter.

27 Claims, 7 Drawing Sheets

US 9,918,731 B2
Page 2

(51) Int. Cl.
*A61B 17/3201* (2006.01)
*A61B 34/30* (2016.01)

(58) Field of Classification Search
CPC ...... A61B 2017/294; A61B 2017/2926; A61B 2017/2933; A61B 2017/2932; A61B 2017/2944; A61B 2017/2934; A61B 2017/2931
USPC ............ 606/205–209, 130; 269/87.2; 81/418
See application file for complete search history.

(56) References Cited

U.S. PATENT DOCUMENTS

| | | | |
|---|---|---|---|
| 4,286,669 A * | 9/1981 | Lasoen | G01L 5/136 172/7 |
| 5,366,477 A * | 11/1994 | LeMarie, III | A61B 17/29 403/336 |
| 5,395,369 A | 3/1995 | McBrayer et al. | |
| 5,674,230 A * | 10/1997 | Tovey | A61B 17/0469 606/139 |
| 5,749,893 A | 5/1998 | Vidal et al. | |
| 5,752,973 A | 5/1998 | Kieturakis | |
| 5,904,702 A | 5/1999 | Ek et al. | |
| 6,132,441 A | 10/2000 | Grace | |
| 6,582,451 B1 | 6/2003 | Marucci et al. | |
| 6,632,160 B2 * | 10/2003 | LaFond | A63B 21/0626 482/132 |
| 6,733,514 B2 | 5/2004 | Miser | |
| 7,214,018 B2 * | 5/2007 | Lussier | B60P 7/14 410/130 |
| 7,578,832 B2 * | 8/2009 | Johnson | A61B 17/1608 606/174 |
| 7,895,757 B1 * | 3/2011 | Huang | A01G 3/02 30/192 |
| 7,963,913 B2 | 6/2011 | Devengenzo et al. | |
| 8,333,780 B1 | 12/2012 | Pedros et al. | |
| 2006/0185464 A1 * | 8/2006 | Telep | F01D 17/16 74/519 |
| 2006/0217706 A1 | 9/2006 | Lau et al. | |
| 2006/0222471 A1 * | 10/2006 | Lussier | B60P 7/14 410/130 |
| 2007/0023477 A1 | 2/2007 | Whitman | |
| 2008/0015631 A1 | 1/2008 | Lee et al. | |
| 2010/0042106 A1 * | 2/2010 | Bryant | A61B 17/8869 606/103 |
| 2010/0057085 A1 | 3/2010 | Holcomb et al. | |
| 2010/0076461 A1 | 3/2010 | Viola et al. | |
| 2010/0198218 A1 | 8/2010 | Manzo | |
| 2011/0087238 A1 | 4/2011 | Wang et al. | |
| 2011/0118778 A1 | 5/2011 | Burbank | |
| 2011/0184459 A1 | 7/2011 | Malkowski et al. | |
| 2011/0196419 A1 | 8/2011 | Cooper | |
| 2012/0215220 A1 | 8/2012 | Manzo et al. | |
| 2013/0018373 A1 | 1/2013 | Lau et al. | |

OTHER PUBLICATIONS

Vertut, Jean, et al., "Teleoperation and Robotics", Robot Technology, vol. 3A, 1986.

* cited by examiner

REMOTELY ACTUATED SURGICAL GRIPPER WITH SEIZE RESISTANCE

CROSS REFERENCE TO RELATED APPLICATIONS

This application claims the benefit pursuant to 35 U.S.C. 119(e) of U.S. Provisional Application No. 61/668,983, filed Jul. 6, 2012, which application is specifically incorporated herein, in its entirety, by reference.

BACKGROUND

Field

Embodiments of the invention relate to the field of surgical instruments; and more specifically, to surgical instruments intended for use in minimally invasive surgeries.

Background

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor. Access to the surgical site may also be via a natural body orifice.

The elongated surgical instruments will generally have an end effector in the form of a surgical tool such as a forceps, a scissors, a clamp, a clip applicator, a needle grasper, or the like at one end of an elongate tube. An actuator that provides the actuating forces to control the end effector is coupled to the other end of the elongate tube. A means of coupling the actuator forces to the end effector runs through the elongate tube. To minimize the size of incision needed for the instrument access port, the elongate tube is generally of a small diameter, in some implementations about 6 millimeters or less, although larger and more complex end effectors (e.g., vessel sealers, surgical staplers, and the like) may require larger diameters, such as 10 or 13 mm. Thus, it is necessary that the means of coupling the actuator forces to the end effector be compact.

It may be desirable that the elongate tube be somewhat flexible to allow the surgical instrument to adapt to the geometry of the surgical access path. In some cases, the elongate tube may be articulated to provide access to a surgical site that is not directly in line with the surgical access port. Articulated surgical instruments may be used for single port surgery in which multiple surgical instruments are inserted through a single cannula. Single port surgery requires that the elongate tube be of a particularly small diameter and that it be capable of being articulated (either actively or passively) after passing through the cannula.

It may be desirable to use wires as the means of coupling the actuator forces to the end effector because of the flexibility they provide and because of the ability of a wire to transmit a significant force, a substantial distance, through a small cross-section. When a wire is used to transmit the actuating forces it is often necessary to provide a mechanical arrangement to translate the push-pull motion of the wire to an open-close motion of an end effector. The small size of the end effector and the unique requirements for surgical instruments significantly increases the difficulty of providing a reliable mechanical arrangement.

In view of the above, it would be desirable to provide an improved apparatus and method for translating a push-pull motion to an open-close motion of a surgical end effector of a surgical instrument intended for use in minimally invasive surgeries with increased reliability.

SUMMARY

A surgical end effector includes a clevis and one or more jaws pivotally coupled to the clevis. At least one jaw includes a slot. An axle assembly includes a bearing axle that rotatably supports a bearing, which may be a plain bearing. An actuator coupling is coupled to the bearing axle. The bearing engages the slot such that pushing and pulling on the actuator coupling causes one jaw to close against the other jaw. The bearing axle and the jaws may be made from materials that are prone to galling and the bearing may be made from a material that resists galling. The slot may include a lip that supports the bearings in a spaced apart relationship. The bearing axle may be less than 1.5 millimeters in diameter and each bearing may be less than 3.0 millimeters in diameter.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
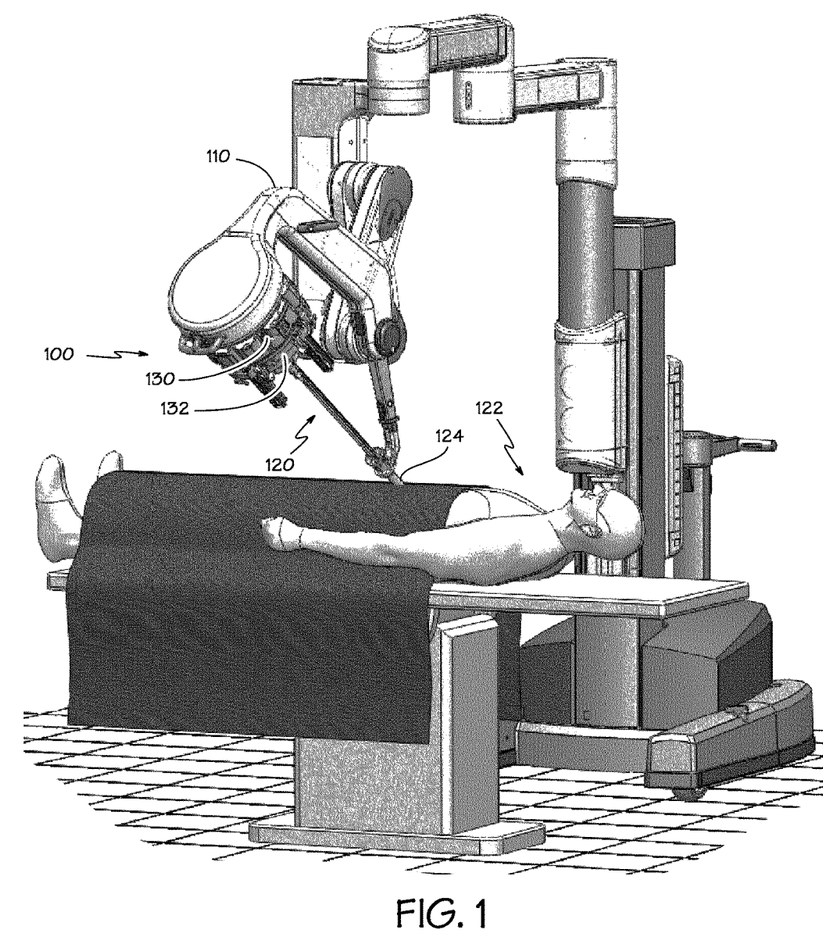
FIG. 1 is a simplified perspective view of a computer-assisted surgical system with a teleoperated surgical instrument inserted through a port in a patient's abdomen.

FIG. 1 is a simplified perspective view of a computer-assisted surgical system 100, in accordance with embodiments of the present invention. The system 100 includes a support assembly 110 mounted to or near an operating table supporting a patient's body 122. The support assembly 110 supports one or more surgical instruments 120 that operate on a surgical site within the patient's body 122. The term "instrument" is used herein to describe a device configured to be inserted into a patient's body and used to carry out surgical procedures. The instrument includes a surgical tool, such as a forceps, a clip applier, a needle driver, a shears, a bipolar cauterizer, a tissue stabilizer or retractor, an anastomosis device, and the like. The surgical tool used with embodiments of the invention provides some form of gripping in which one part of the tool opens and closes against another part.

The simplified perspective view of the system 100 shows only a single instrument 120 to allow aspects of the invention to be more clearly seen. A functional computer-assisted surgical system would further include a vision system that enables the surgeon to view the surgical site from outside the patient's body 122. The vision system can include a video monitor for displaying images received by an optical device provided at a distal end of one of the surgical instruments 120. The optical device can include a lens coupled to an optical fiber or a lens system which carries the detected images to an imaging sensor (e.g., a CCD or CMOS sensor) outside of the patient's body 122. Alternatively, the imaging sensor may be provided at the distal end of the surgical instrument 120, and the signals produced by the sensor are transmitted along a lead or wirelessly for display on the monitor. An illustrative monitor is the stereoscopic display on the surgeon's cart in the da Vinci® Surgical System, commercialized by Intuitive Surgical, Inc., of Sunnyvale, Calif.

A functional computer-assisted surgical system would further include a control system for controlling the insertion and articulation of the surgical instruments 120. This control may be effectuated in a variety of ways, depending on the degree of control desired, the size of the surgical assembly, and other factors. In some embodiments, the control system includes one or more manually operated input devices, such as a joystick, exoskeletal glove, or the like. These input devices control servo motors which, in turn, control the articulation of the surgical assembly. The forces generated by the servo motors are transferred via drivetrain mechanisms, which transmit the forces from the servo motors generated outside the patient's body 122 through an intermediate portion of the elongate surgical instrument 120 to a portion of the surgical instrument inside the patient's body 122 distal from the servo motor. Persons familiar with telemanipulative, teleoperative, and telepresence surgery will know of systems such as the da Vinci® Surgical System and the Zeus® system originally manufactured by Computer Motion, Inc., and various illustrative components of such systems.

The surgical instrument 120 is shown inserted through an entry guide cannula 124, e.g., a single port in the patient's abdomen. A functional computer-assisted surgical system may provide an entry guide manipulator, which may be part of the support system 110, and an instrument manipulator (discussed below). The entry guide 124 is mounted onto the entry guide manipulator, which includes a teleoperated positioning system for positioning the distal end 126 of the entry guide 124 at the desired target surgical site. The teleoperated positioning system may be provided in a variety of forms, such as a serial link arm having multiple degrees of freedom (e.g., six degrees of freedom) or a jointed arm that provides a stationary remote center of motion (due to either hardware or software constraints) and which is positioned by a setup joint mounted onto a base. Alternatively, the entry guide manipulator may be manually maneuvered so as to position the entry guide 124 in the desired location. In some telesurgical embodiments, the input devices that control the manipulator(s) may be provided at a location remote from the patient (outside the room in which the patient is placed). The input signals from the input devices are then transmitted to the control system, which, in turn, manipulates the manipulators 130 in response to those signals. The instrument manipulator may be coupled to the entry guide manipulator such that the instrument manipulator 130 moves in conjunction with the entry guide 124.

The surgical instrument 120 is detachably connected to the teleoperated instrument manipulator 130 so that the surgical instrument can be easily removed and replaced with another surgical instrument. The teleoperated manipulator includes a coupler 132 to transfer controller motion from the teleoperated manipulator to the surgical instrument 120. The instrument manipulator 130 may provide a number of controller motions which the surgical instrument 120 may translate into a variety of movements of the end effector on the surgical instrument such that the input provided by a surgeon through the control system is translated into a corresponding action by the surgical instrument.

Figure 2:
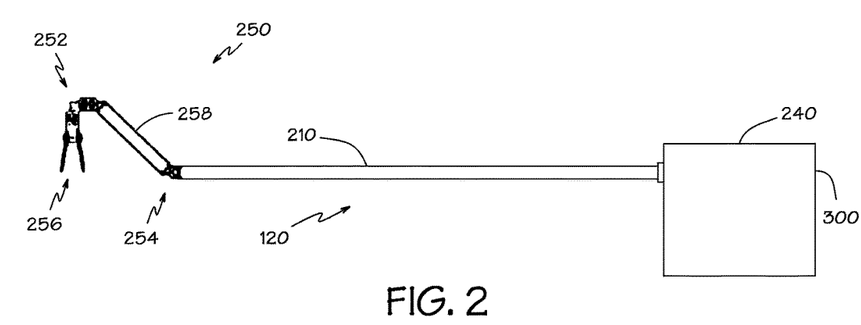
FIG. 2 is a plan view of a surgical instrument for use with a teleoperated manipulator.

FIG. 2 is a plan view of an illustrative embodiment of the surgical instrument 120, comprising a distal portion 250 and a proximal control mechanism 240 coupled by a shaft or elongate tube 210. The proximal control mechanism 240 provides a means for receiving a controller motion (e.g., a motion generated by a teleoperated servo motor). The distal portion 250 of the surgical instrument 120 can provide any of a variety of surgical devices as an end effector such as the forceps shown, a clip applier, a needle driver, a shears, a bipolar cauterizer, a tissue stabilizer or retractor, an anastomosis device, and the like. Many of the surgical devices that may be provided as an end effector have a pair of jaws 256 having the ability to be open and closed with a jaw-like motion. This requires that a controller motion provided by the instrument manipulator 130 be transmitted through the elongate tube 210 to effect the opening and closing of the jaws 256.

The instrument shown includes an articulating section 258 that is coupled to the elongate tube 210 by a flexible joint 254. The end effector is coupled to the articulating section 258 by another flexible joint 252. This arrangement allows the end effector to be displaced from the longitudinal axes of the cannula and the elongate tube 210, which is supported in the cannula. This arrangement also increases the difficulty of transmitting the controller motion from the proximal control mechanism 240 to the end effector. If a flexible wire is used as an actuating link to transmit the controller motion to open and close the jaws of the end effector, the jaws will generally be opened by pushing on the wire since less force can delivered when pushing and opening the jaws will generally require less force than closing the jaws. It is important that the end effector be designed to minimize the pushing force required to allow the pushing force to be delivered by a relatively flexible wire. In this description, the term wire should be broadly construed to include single strand and multi-strand elements capable of longitudinally transmitting push, pull, or combined push and pull force through an elongate surgical instrument shaft (e.g., a tube), and such elements may be relatively stiff (resistant to bending) or relatively flexible (e.g., for routing through a single or multiple degree of freedom wrist).

Figures 3A, 3B, 4:
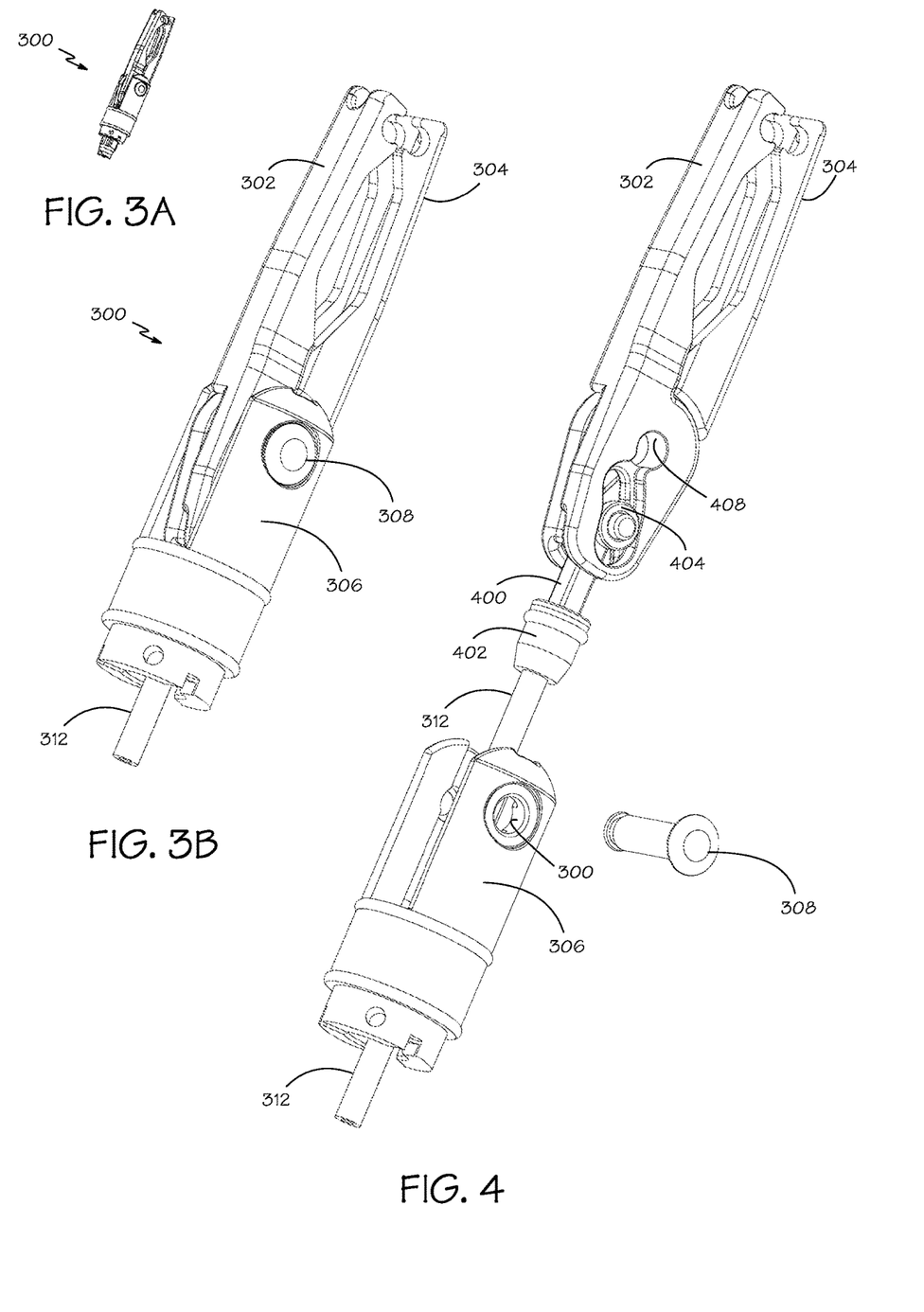
FIG. 3A is a pictorial view of a surgical end effector at approximately an actual size.
FIG. 3B is a pictorial view of the surgical end effector substantially enlarged.
FIG. 4 is a partially disassembled view of the surgical end effector of FIG. 3.

FIG. 3A shows a clip applier end effector 300 that embodies the present invention at approximately the actual size of 6 mm in diameter. The small size of the end effector greatly increases the challenges of designing a workable mechanism. The limitations imposed by surgical usage, discussed below, increase these challenges still further.

FIG. 3B shows the clip applier end effector 300 greatly enlarged so that the details of construction can be seen. The end effector 300 includes a clevis 306 that is coupled to the distal end of the elongate tube 210. An actuating link 312 extends through the elongate tube 210 between the distal end and the proximal end. The actuating link 312 may be a flexible connector such as a wire, cable, thin rod, or the like. A first jaw 302 and a second jaw 304 are coupled to the clevis by a pivot 308. As disclosed below, the use of a clevis to support the jaws is optional, and persons of skill in the art will know various jaw arrangements. Thus, descriptions of clevis-based implementations may apply to other jaw arrangements when practical. It should be understood, however, that the clevis-based implementations are important in small instrument diameter implementations in which two jaws both move towards each other.

FIG. 4 shows the clip applier end effector 300 partially disassembled to allow further details of the construction to be seen. The pivot 308 couples the first jaw 302 and the second jaw 304 to the clevis 306 by passing through holes in the clevis and jaws. The pivot 308 both retains the jaws 302, 304 in the clevis 306 and provides an axle on which the jaws rotate. The actuating link 312 is attached to an axle assembly 400 described in detail below. An optional resilient seal may be molded onto one end of the axle assembly 400 to stop the flow of fluid from the surgical site into the elongate tube 210.

Figure 5:
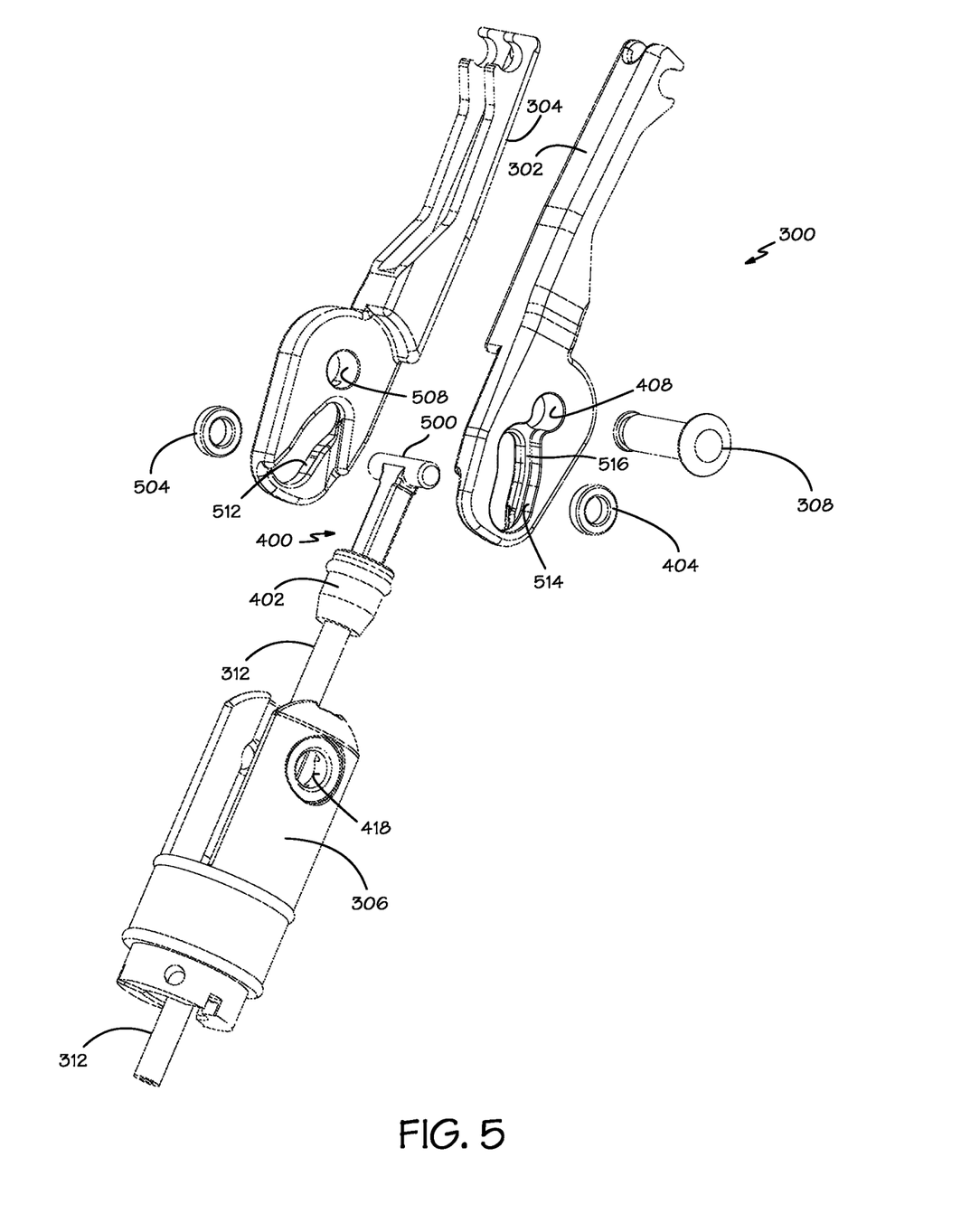
FIG. 5 is an exploded view of the surgical end effector of FIG. 3.

FIG. 5 shows the clip applier end effector 300 in an exploded view to allow additional details of the construction to be seen. As can be seen, the pivot 308 passes through a hole 418 in the clevis, a first pivot hole 408 in the first jaw 302, and second pivot hole 508 in the second jaw 304.

The axle assembly 400 includes a bearing axle 500 that rotatably supports two bearings 404, 504 disposed at opposing ends of the bearing axle so that the bearings rotate on the axle. An actuator coupling 502 is coupled to the actuating link 312 and to the bearing axle substantially at a midpoint between the first and second bearings. If the actuating link 312 is of a stranded construction, the actuating link may include an aglet attached to the end of the actuating link where it is attached to the axle assembly 400 to keep the strands of the actuating link from splaying out. The aglet may be in the form of a thin metal fitting swaged onto the actuating link. The actuator coupling 502 may provide a hollow section that receives the end of the actuating link which may then be attached to the axle assembly 400 such as by welding, soldering, or crimping. The bearing axle 500 may be pulled away from the jaws 302, 304 or pushed toward the jaws by pushing and pulling on the actuating link 312 using the proximal control mechanism 240 at the proximal end of the elongate tube 210.

The first jaw 302 includes a first slot 514, and the second jaw 304 includes a second slot 512. Each of the two bearings 404, 504 engages one of the slots such that the controller motion pushing and pulling on the actuating link 312 at the proximal end causes the jaws 302, 304 to rotate about the pivot 308 in opposition to one another. The outer surface of each of the bearings presses against a sidewall in their respective slots so that each bearing rolls along its respective sidewall as the jaws pivot. The bearings engage against opposite sidewalls in the slots, depending if the jaws are pivoting open or closed. In the illustrated mechanism, the sidewall surfaces are flat, although they may optionally be lengthwise convex, concave, channeled, or railed to help keep matching shaped bearing surfaces aligned with the sidewall surfaces as the bearings travel in the slots.

Figure 6A:
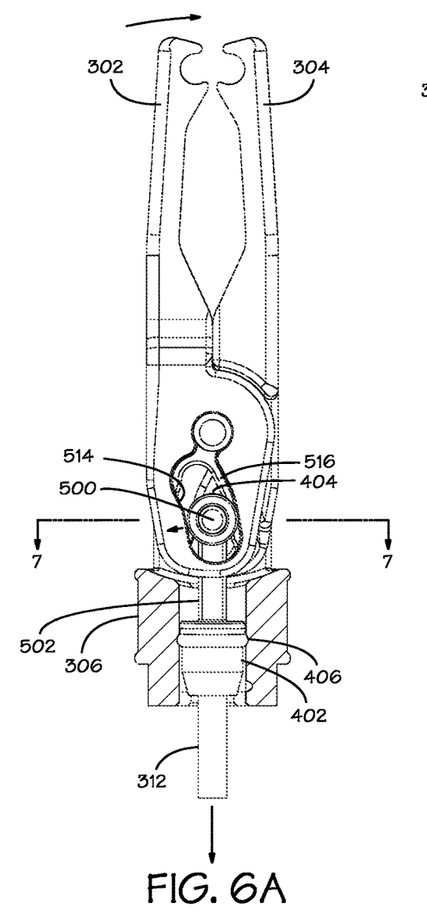
FIG. 6A is a front view of the surgical end effector in a closed position with a front portion of the clevis cut away to allow certain details to be seen more clearly.
Figure 6B:
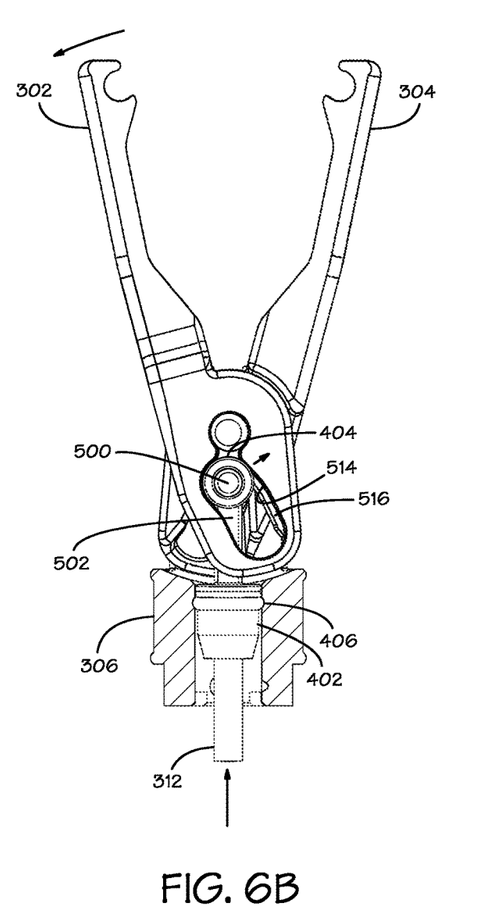
FIG. 6B is a front view of the surgical end effector in an open position.

FIG. 6A is an orthogonal view of the end effector 300 with jaws in a closed position, and FIG. 6B is an orthogonal view of the same end effector with jaws in an open position. It will be seen in FIG. 6A that as the bearing axle 500 is pulled away from the jaws 302, 304, the bearings 404 push against the walls of the slots 514 in the jaws 302 and cause the ends of the jaws to rotate about the pivot (the pivot pin 308 that passes through the pivot holes 408, 508 is not shown in this figure for clarity) toward each other with a closing action. The slot may be curved as shown to increase the closing force as the distance between the bearing axle 500 and the jaws 302, 304 increases. Conversely, it will be seen in FIG. 6B that as the bearing axle 500 is pushed toward the jaws 302, 304, the bearings 404 push against the walls of the slots 514 in the jaws 302 and cause the ends of the jaws to rotate about the pivot away from each other with an opening action.

The stringent requirements imposed by the surgical environment creates several challenges in providing an effective mechanism to open and close the jaws 302, 304. One requirement is that the end effector be of a small size so that it can pass through the cannula, which may require that the end effector be no more than 5 mm in diameter when closed although the invention is applicable to larger end effectors as well. It is also desirable that the end effector remain relatively compact throughout its range of motion. All parts of the end effector must be made from materials that are acceptable for use in a surgical application. The mechanism must be able to withstand surgical cleaning and sterilization (e.g., withstand autoclave sterilization) and be able to function without the use of lubricants. Above all, the end effector must function with a high degree of reliability and resistance to breakage.

The jaws are generally arranged such that the pivot point is substantially closer to the end containing the slots so that the slotted end does not become unduly large when the jaws are opened. This means that closing force at the working end of the jaws is a fraction of the force applied by the bearings to close the jaws. If a plain pin is used to open and close the jaws by sliding in the slot, the closing forces create a high frictional resistance to the applied forces to push the pin toward the jaws to open them. This may cause the actuating link to buckle because it is not possible to apply a high force by pushing on a flexible actuating link.

It has been found that the use of bearings 404, 504 rotatably supported on an axle 500 rather than using a plain pin to actuate the jaws 302, 304 of the end effector 300 reduces the friction against the jaw slots 512, 514 and increases the reliability of opening the jaws. Reducing the friction against the jaw slots 512, 514 also reduces the amount of tension required in the actuating link 312 to achieve a given closing force in the jaws. The use of bearings 404, 504 allows the mechanical advantage of the jaws to be increased by use of a smaller angle between the jaw slots 512, 514. The bearings allow the increased mechanical advantage without the jaws getting stuck or locked as readily as they would using a plain pin to actuate the jaws. The bearings rotate on the axle without lubricant because the instrument is sterilized by autoclaving, which removes lubricant.

Figure 7:
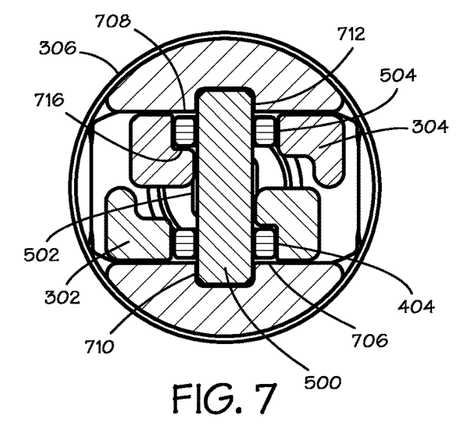
FIG. 7 is a cross-section view of the surgical end effector taken along line 7-7 in FIG. 6A.

FIG. 7 shows a cross section of the end effector taken along line 7-7 in FIG. 6A. The slot 514 in each jaw 302, 304 includes a lip 516, 716 that supports the bearing 404, 504 in a spaced apart relationship to the actuator coupling 502. An inner wall 706, 708 of the clevis 306 adjacent the bearing 404, 504 retains the bearing on the bearing axle 500. Thus the bearing 404, 504 is held captive on the bearing axle 500 between the lip 516, 716 and the wall 706, 708 of the clevis 306.

The inner walls 706, 708 of the clevis 306 may provide a groove 710, 712 that receives the outer ends of the bearing axle 500 such that the bearing axle extends through and beyond the bearing 404, 504. The grooves 710, 712 in the clevis 306 also stabilize the axle assembly 400 and constrain the bearing axle 500 to a push-pull motion.

Figure 8:
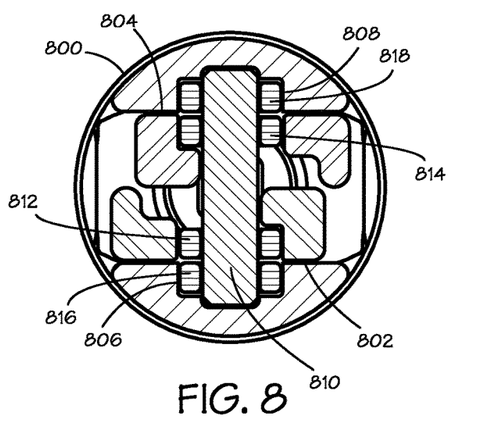
FIG. 8 is cross-section view of another surgical end effector corresponding to the view in FIG. 7.

FIG. 8 shows a cross section of another end effector corresponding to the view in FIG. 7. In this embodiment, the inner walls 802, 804 of the clevis 800 provide grooves 806, 808 that receive the outer ends of the bearing axle 810 and third and fourth bearings 814, 818 that support the outer ends of the in the clevis grooves. The bearing axle extends through and beyond the first and second bearings 812, 816 and through the third and fourth bearings 814, 818.

Figure 9:
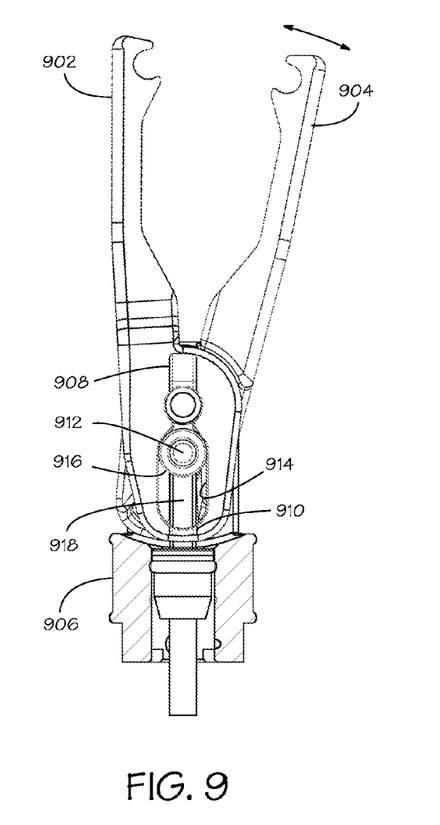
FIG. 9 is a front view of yet another surgical end effector in an open position with a front portion of the clevis cut away to allow certain details to be seen more clearly.

FIG. 9 shows an orthogonal view of yet another surgical end effector. This end effector provides one moveable jaw 904 and one fixed jaw 902. The moveable jaw 904 operates as described for the previously described end effectors. The fixed jaw 902 remains fixed in position relative to the clevis 906.

The fixed jaw 902 may be fixed with respect to the clevis 906 in any of a variety of ways. In the embodiment illustrated a raised ridge 908, 910 is provided on the fixed jaw 902. The raised ridge 908, 910 engages the slot in the clevis 906 that receives the end of the axle 912. The pivot (not shown) holds the fixed jaw 902 in the clevis 906 and the raised ridge 908, 910 prevents the fixed jaw from rotating thus fixing the jaw with respect to the clevis.

The fixed jaw 902 includes an elongated slot 914 that receives the bearing 916 mounted on the axle 912. The elongated slot 914 includes straight, long walls that are parallel to the motion of the bearing 916 when the fixed jaw 902 is fixed to the clevis 906. Thus movement of the bearing 916 does not create any forces on the elongated slot 914 that would attempt to rotate the fixed jaw 902 about the pivot. However, the forces applied to rotate the moveable jaw 904 about the pivot create reaction forces that twist the axle around the longitudinal axis of the actuator coupling 918 that is coupled to the bearing axle substantially at a midpoint. The elongated slot 914 of the fixed jaw 902 resist the reaction forces and prevents twisting of the axle.

Figure 10:
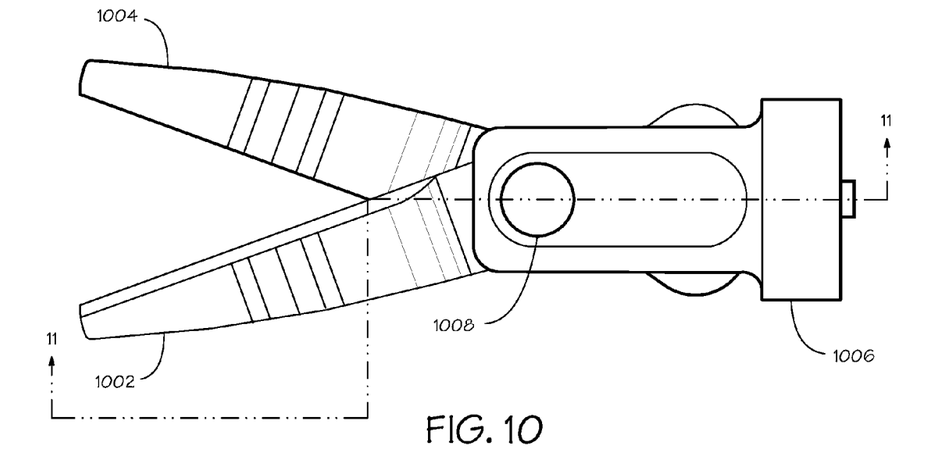
FIG. 10 is a front view of still another surgical end effector in an open position.

FIG. 10 is a front view of still another surgical end effector in an open position. This surgical end effector illustrates a construction that may be particularly suited to surgical scissors and similar instruments. The surgical end effector includes two cutting blades 1002, 1004 that are supported by a pivot 1008 in a clevis 1006.

Figure 11:
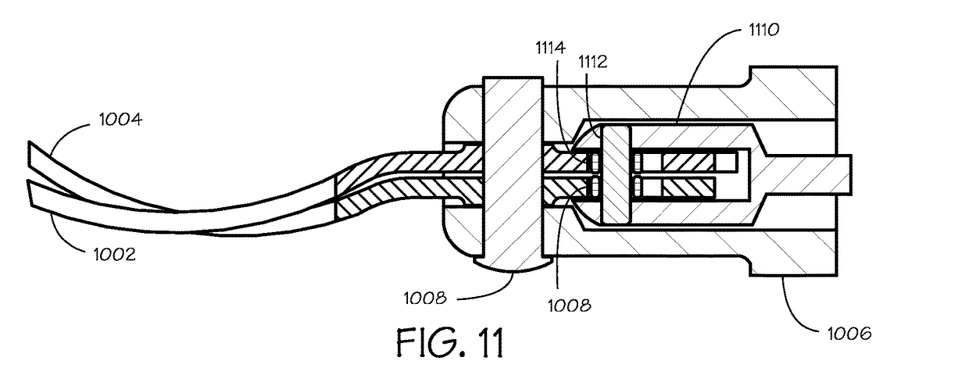
FIG. 11 is a cross-section view of the surgical end effector taken along line 11-11 in FIG. 10.

FIG. 11 is a cross-section view of the surgical end effector taken along line 11-11 in FIG. 10. As can be seen in this view, the two cutting blades 1002, 1004 may be curved. It will also be seen that the blades are formed such that they are elastically deformed as the blades are closed. This ensures that there is a substantial force that holds the two cutting blades 1002, 1004 in contact at the point where the blades intersect, a point which moves away from the portion of the blades closest to the pivot 1008 and toward the tips of the blades as the blades are closed. It is important that the blades be held together with a substantial force at the point where the blades are cutting to permit thin but tough tissues to be cut cleanly. If there is insufficient force urging the blades together the tissue may wrap around a cutting edge and become wedged between the blades, and the blades cannot properly shear the tissue.

It may be advantageous to use an actuator coupling 1110 that supports a bearing axle 1112 adjacent the ends of the bearing axle. This permits the two jaws or blades 1002, 1004 of the surgical end effector to have mating surfaces, such as the cutting edges, that are in close proximity throughout their length. In some embodiments, the bearing axle may extend beyond the actuator coupling into grooves in the clevis to provide additional support for the bearing axle and/or to prevent the actuator coupling from rotating.

Figure 12:
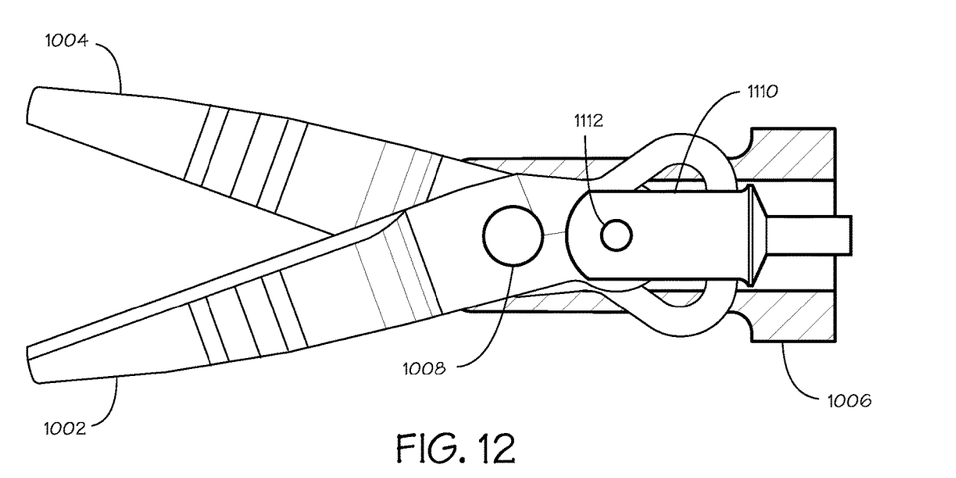
FIG. 12 is a front view of the surgical end effector of FIG. 10 with a front portion of the clevis cut away to allow certain details to be seen more clearly.

FIG. 12 is a front view of the surgical end effector of FIG. 10 with a front portion of the clevis cut away to allow the actuator coupling 1110 and the bearing axle 1112 to be seen from the front.

Figure 13:
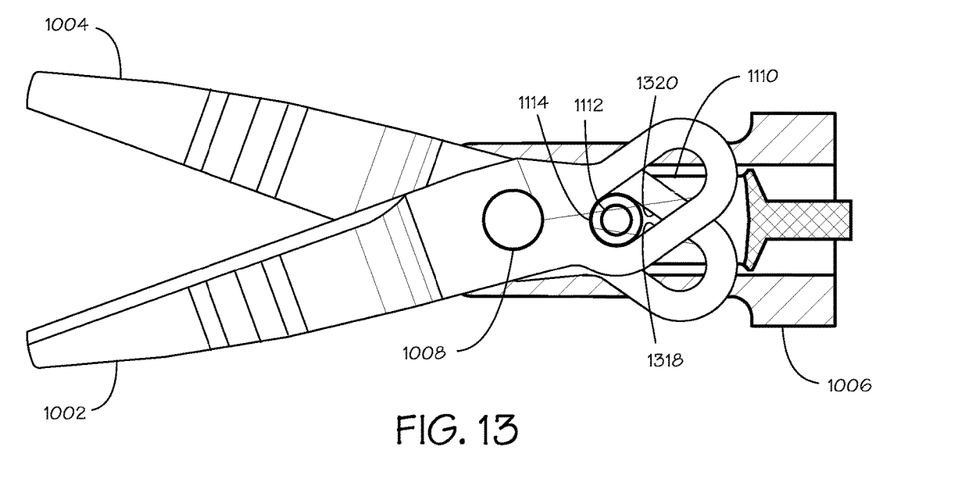
FIG. 13 is a front view of the surgical end effector of FIG. 10 with a front portion of the actuator coupling cut away to allow additional details to be seen more clearly.

FIG. 13 is a front view of the surgical end effector of FIG. 10 with a front portion of the actuator coupling 1110 cut away to allow the bearing axle 1112 to be seen from the front.

As in previous embodiments, a first bearing 1114 and a second bearing 1116 are rotatably supported on the bearing axle 1112. The first bearing 1114 engages a first slot 1318 and the second bearing 1116 engages a second slot 1320 such that pushing and pulling on the actuator coupling 1110 causes the first and second jaws 1002, 1004 to rotate about the pivot 1008 in opposition to one another.

In the embodiment illustrated, the two bearings are directly adjacent one another on the bearing axle 1112. In other embodiments, there may be provisions for holding the two bearings apart from one another on the bearing axle. For example, the bearing axle could include a ridge between the two bearings. As another example, an additional bearing that does not engage the slots may be provided between the two bearings that engage the slots.

In the embodiment illustrated, the two bearings are each directly adjacent one of the jaws. In other embodiments, there may be provisions for holding each bearing apart from the adjacent jaw. For example, a spring washer, such as a Belleville washer, may be provided on the bearing axle between the bearing and the adjacent jaw. The bearing axle may extend beyond the actuator coupling into grooves in the clevis to retain the spring washer. Additional bearings may be provided to support the bearing axle in the grooves in the inner walls of the clevis.

Figure 14:
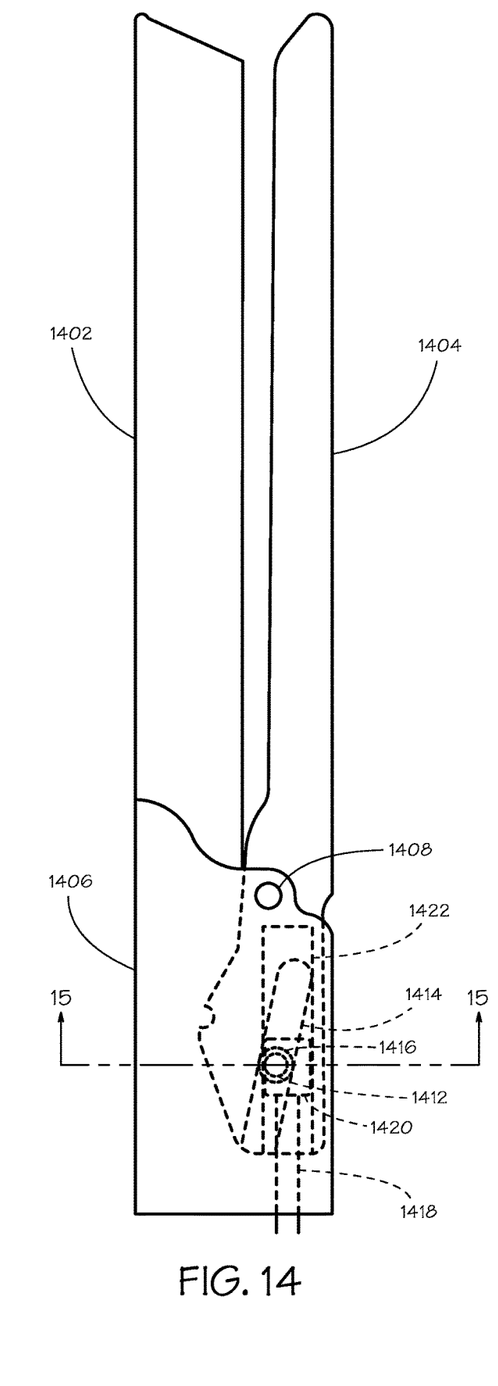
FIG. 14 shows an orthogonal view of yet another surgical end effector.

FIG. 14 shows an orthogonal view of yet another surgical end effector. This end effector provides one moveable jaw 1404 and one fixed jaw 1402. The moveable jaw 1404 is coupled to a clevis 1406 by a pivot pin (not shown) that passes through holes 1408 in the clevis and the moveable jaw.

The fixed jaw 1402 remains fixed in position relative to the clevis 1406. The fixed jaw 1402 may be fixed with respect to the clevis 1406 in any of a variety of ways, including forming the fixed jaw 1402 and clevis 1406 from a single piece, or optionally from two mating pieces. In the embodiment illustrated the fixed jaw 1402 is fabricated as an extension of the clevis.

The fixed jaw 1402 and/or the clevis 1406 includes an elongated slot 1422 that receives an axle block 1420 that supports an axle 1412. A bearing 1416 is mounted on the axle 1412 in each side of the block. The axle block 1420 is moved within the elongated slot 1422 by an actuating link 1418.

Figure 15:
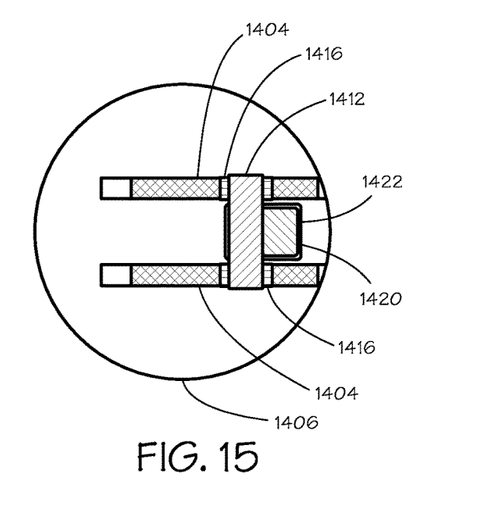
FIG. 15 is a cross-section view of the surgical end effector taken along line 15-15 in FIG. 14.

FIG. 15 is a cross-section of the surgical end effector taken along line 15-15 in FIG. 14. Each bearing 1416 engages an elongated slot 1414 in the moveable jaw 1404. As seen in the cross-section, the moveable jaw 1404 wraps around the portion of the clevis 1406 that provides the elongated slot 1422 in which the axle block 1420 slides. By supporting the axle 1412 in the axle block 1420 which is in turn supported by the elongated slot 1422 in the clevis 1406, the two bearings 1416 acting on the moveable jaw 1404 can generate a substantial force and a closely controlled motion that may be advantageous for certain types of surgical end effector such as staplers.

It will be appreciated that the use of bearings requires the use of a bearing axle having a smaller diameter than a plain pin since the outer diameter of the bearings will have substantially the diameter of a plain pin. It may be advantageous to use plain bearings because they provide a large inside diameter relative to the outside diameter and allow the use of a larger bearing axle. Plain bearings can withstand the applied loads for closing the jaws, which other bearings, such as ball bearings, of this size cannot. An exemplary embodiment of an end effector may have a bearing axle of less than 1.5 millimeters in diameter and bearings of less than 3.0 millimeters in diameter.

It will be appreciated that there will still be sliding friction when using a plain bearing. The use of a plain bearing transforms the friction against the slot from sliding friction to rolling friction, which is much lower, but it also creates a new point of sliding friction between the bearing and the axle. However, the speed of the motion between the bearing and the axle relative to the speed of the motion of pin sliding against the slot is reduced by the ratio of the axle diameter to the bearing outer diameter, thus reducing the sliding friction when a bearing is used.

It is desirable to fabricate the parts of the end effector from a material that is strong, corrosion resistant, and highly machinable so that small, intricately shaped parts can be effectively fabricated. Martensitic stainless steels are extremely strong and tough, as well as highly machinable. Precipitation-hardening martensitic stainless steels have better corrosion resistance than other martensitic stainless steels. The corrosion resistance of precipitation-hardening martensitic stainless steels are comparable to austenitic varieties. Precipitation-hardening martensitic stainless steels can be precipitation hardened to even higher strengths than the other martensitic grades. The most common precipitation-hardening martensitic stainless steel, 17-4PH, uses about 17% chromium and 4% nickel and is a suitable material for fabricating the parts of the end effector.

One drawback of using many metals, including 17-4PH stainless steel, is the susceptibility to galling. Galling occurs when localized high pressure contact occurs between two metal surfaces causing adhesion and transfer of material from one surface to the other. Galling leads to rough surfaces and a dramatic increase in the sliding friction between the surfaces. A plain pin used to open and close the jaws by sliding in the slot is highly prone to failure due to galling. The addition of the plain bearing which rolls in the slot reduces the effects of galling at the slot surface. However, there is still sliding friction between the plain bearing and the bearing axle. The friction effects are reduced because the speed between the sliding surfaces is reduced by the ratio of the outer to inner diameters of the bearing, making the speed between the sliding surfaces of an exemplary embodiment about one-half that of a comparable plain pin.

The plain bearing is easier to fabricate, and it only requires a good compressive strength. Thus it is possible to fabricate the plain bearing from materials that would not be suitable for fabricating the remaining parts of the end effector. This permits the plain bearing to be fabricated from a material that improves the resistance to galling of the actuating mechanism of the end effector.

Resistance to galling may be evaluated by a test method comprised of rotation of a polished cylindrical section or button of a first material for one revolution under pressure against a polished block surface of a second material in a standard Brinell hardness machine. The first and second materials may be the same or different materials. The unit contact pressure between the two materials just sufficient to cause galling under these test conditions provides a quantitative measure of the resistance to galling for that pair of materials, which may be termed "threshold galling stress."

A button specimen may be prepared by drilling a countersunk hole to accommodate most of the exposed Brinell hardness ball. The button specimen may then be mounted in Bakelite and polished to a 600 grit finish in a grinder/polisher, such as a Buehler EcoMet® Grinder-Polisher and AutoMet® Power Head, to obtain a relatively flat test surface, with the edges slightly rounded. The button may then be broken out of the Bakelite, and the edges hand deburred. A block specimen may be prepared by grinding parallel on two sides and hand-polishing to a 3/0 emery grit finish, equivalent to a 600 grit finish. Both the button and block specimens may be degreased by wetting with acetone.

The hardness ball is lubricated just prior to testing. The button is hand-rotated slowly at a predetermined load for one revolution and then examined under at least 7× magnification for galling. If galling is not observed (i.e. absence of metal build-up, usually at the end of a groove), new specimens are tested at successively higher loads until galling is first observed. Confirmation may be obtained by testing an additional pair of specimens at a higher load. Since light loads do not cause full area contact due to the rounded button edges, the actual contact area is measured for computing the threshold galling stress. The threshold galling stress is selected as the stress midway between the highest non-galled stress and the stress where galling was first observed.

Two surfaces of 17-4PH stainless steel provide a threshold galling stress of about 2 kilopounds per square inch (kpsi). 17-4PH stainless steel in combination with Nitronic 60® stainless steel, as supplied by Electralloy of Oil City, Pa. under license from Armco Inc., provides a threshold galling stress in excess of 50 kpsi, the limit of the testing equipment. Thus Nitronic 60® stainless steel is a suitable material for fabricating the plain bearing for the inventive end effector.

Other materials that provide a high threshold galling stress in combination with the axle material may be also used for the plain bearing. For example, a threshold galling stress between the material used for the bearing and the material used for the bearing axle of greater than 35 kpsi would be desirable. For comparison, a threshold galling stress between the material used for the jaws and the material used for the bearing axle may be less than 10 kpsi, which is undesirable with regard to galling resistance. The plain bearing may also be made from a non-metallic material that provides the necessary compressive strength and galling resistance, such as a ceramic or jewel bearing.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. A surgical end effector comprising:
    a clevis comprising two walls, each wall of the two walls having an inward-facing surface;
    a jaw comprising an outward-facing surface, a slot comprising an inward-facing portion and an outward-facing portion, and a pivot hole comprising an inward-facing portion and an outward-facing portion,
        the outward-facing surface of the jaw being adjacent the inward-facing surface of a first one of the two walls,
        the outward-facing portion of the slot being enlarged to form a lip between the inward-facing and outward-facing portions of the slot, and
        the outward-facing portion of the slot being open to the outward-facing portion of the pivot hole;
    a pivot that passes through the two walls of the clevis and the pivot hole of the jaw; and
    an axle assembly that includes
        an actuator coupling,
        a bearing axle at an end of the actuator coupling and extending from the actuator coupling through the inward-facing and outward-facing portions of the slot, and
        a bearing rotatably supported by the bearing axle in the outward-facing portion of the slot, the bearing being axially constrained by the lip of the slot.

2. The surgical end effector of claim 1 wherein the bearing axle is less than 1.5 millimeters in diameter and the bearing is less than 3.0 millimeters in diameter.

3. The surgical end effector of claim 1 wherein the bearing is a plain bearing.

4. The surgical end effector of claim 1 wherein:
    the bearing axle is made from a first material;
    the jaw is made from a second material wherein a first threshold galling stress between the first material and the second material is less than 10 kpsi; and
    the bearing is made from a third material wherein a second threshold galling stress between the first material and the third material is greater than 35 kpsi.

5. The surgical end effector of claim 4 wherein a third threshold galling stress between the second material and the third material is greater than 35 kpsi.

6. The surgical end effector of claim 1 wherein the lip supports the bearing in a spaced apart relationship to the actuator coupling.

7. The surgical end effector of claim 1 further comprising a second jaw comprising a second slot and a second bearing rotatably supported by the bearing axle in the second slot.

8. The surgical end effector of claim 7 wherein each wall of the two walls comprises a groove that receives one of two ends of the bearing axle.

9. The surgical end effector of claim 8 further comprising a third bearing and a fourth bearing that support the two ends of the bearing axle in the grooves in the two walls of the clevis.

10. The surgical end effector of claim 7 wherein the pivot further passes through a second pivot hole in the second jaw to couple the second jaw to the clevis and wherein pushing and pulling on the actuator coupling causes the jaw to rotate about the pivot in opposition to the second jaw.

11. A minimally invasive surgical instrument comprising:
    an elongate shaft having a distal end, a proximal end, and a longitudinal axis extending between the distal end and the proximal end;
    an end effector having a clevis coupled to the distal end of the elongate shaft, the clevis comprising two walls, each wall of the two walls having an inward-facing surface;
    a jaw comprising an outward-facing surface, a slot comprising an inward-facing portion and an outward-facing portion, and a pivot hole comprising an inward-facing portion and an outward-facing portion, the outward-facing surface of the jaw being adjacent the inward-facing surface of a first one of the two walls,
the outward-facing portion of the slot being enlarged to form a lip between the inward-facing and outward-facing portions of the slot, and
the outward-facing portion of the slot being open to the outward-facing portion of the pivot hole;
a pivot that passes through the two walls of the clevis and the pivot hole of the jaw;
an actuating link extending through the elongate shaft between the distal end and the proximal end; and
an axle assembly that includes
an actuator coupling,
a bearing axle at an end of the actuator coupling and extending from the actuator coupling through the inward-facing and outward-facing portions of the slot, and
a bearing rotatably supported by the bearing axle in the outward-facing portion of the slot, the bearing being axially constrained by the lip of the slot.

12. The surgical instrument of claim 11 wherein the bearing axle is less than 1.5 millimeters in diameter and the bearing is less than 3.0 millimeters in diameter.

13. The surgical instrument of claim 11 wherein the bearing is a plain bearing.

14. The surgical instrument of claim 11 wherein:
the bearing axle is made from a first material;
the jaw is made from a second material wherein a first threshold galling stress between the first material and the second material is less than 10 kpsi; and
the bearing is made from a third material wherein a second threshold galling stress between the first material and the third material is greater than 35 kpsi.

15. The surgical instrument of claim 14 wherein a third threshold galling stress between the second material and the third material is greater than 35 kpsi.

16. The surgical instrument of claim 11 wherein the lip supports the bearing in a spaced apart relationship to the actuator coupling.

17. The surgical instrument of claim 11 wherein each wall of the two walls comprises a groove that receives one of two ends of the bearing axle.

18. The surgical instrument of claim 17 further comprising a third bearing and a fourth bearing that support the two ends of the bearing axle in the grooves in the two walls of the clevis.

19. A minimally invasive surgical instrument comprising:
means for receiving a controller motion;
an elongate shaft coupled to the means for receiving the controller motion at a proximal end of the elongate shaft, the elongate shaft having a distal end opposite the proximal end along a longitudinal axis extending between the distal end and the proximal end;
an end effector having a clevis coupled to the distal end of the elongate shaft, the clevis comprising two walls, each wall of the two walls having an inward-facing surface;
a jaw comprising an outward-facing surface, a slot comprising an inward-facing portion and an outward-facing portion, and a pivot hole comprising an inward-facing portion and an outward-facing portion,
the outward-facing surface of the jaw being adjacent the inward-facing surface of a first one of the two walls,
the outward-facing portion of the slot being enlarged to form a lip between the inward-facing and outward-facing portions of the slot, and
the outward-facing portion of the slot being open to the outward-facing portion of the pivot hole;
a pivot that passes through the two walls of the clevis and the pivot hole of the jaw;
an actuating link extending through the elongate shaft between the distal end and the proximal end; and
an axle assembly that includes
an actuator coupling;
a bearing axle at an end of the actuator coupling and extending from the actuator coupling through the inward-facing and outward-facing portions of the slot, and
a bearing rotatably supported by the bearing axle in the outward-facing portion of the slot, the bearing being axially constrained by the lip of the slot.

20. The surgical instrument of claim 19 wherein the bearing axle is less than 1.5 millimeters in diameter and the bearing is less than 3.0 millimeters in diameter.

21. The surgical instrument of claim 19 wherein the bearing is a plain bearing.

22. The surgical instrument of claim 19 wherein:
the bearing axle is made from a first material;
the jaw is made from a second material wherein a first threshold galling stress between the first material and the second material is less than 10 kpsi; and
the bearing is made from a third material wherein a second threshold galling stress between the first material and the third material is greater than 35 kpsi.

23. The surgical instrument of claim 22 wherein a third threshold galling stress between the second material and the third material is greater than 35 kpsi.

24. The surgical instrument of claim 19 wherein the lip supports the bearing in a spaced apart relationship to the actuator coupling.

25. The surgical instrument of claim 19 wherein each wall of the two walls comprises a groove that receives one of two ends of the bearing axle.

26. The surgical instrument of claim 25 further comprising a third bearing and a fourth bearing that support the two ends of the bearing axle in the grooves in the two walls of the clevis.

27. A minimally invasive surgical instrument comprising:
an elongate shaft having a distal end, a proximal end, and a longitudinal axis extending between the distal end and the proximal end;
an end effector having a clevis coupled to the distal end of the elongate shaft, the clevis comprising two walls, each wall of the two walls having an inward-facing surface;
a jaw made from a first material, the jaw comprising an outward-facing surface, a slot comprising an inward-facing portion and an outward-facing portion, and a pivot hole comprising an inward-facing portion and an outward-facing portion,
the outward-facing surface of the jaw being adjacent the inward-facing surface of a first one of the two walls,
the outward-facing portion of the slot being enlarged to form a lip between the inward-facing and outward-facing portions of the slot, and
the outward-facing portion of the slot being open to the outward-facing portion of the pivot hole;
a pivot that passes through the two walls of the clevis and the pivot hole of the jaw;

an actuating link extending through the elongate shaft between the distal end and the proximal end; and an axle assembly that includes
- an actuator coupling,
- a bearing axle at an end of the actuator coupling made from a second material and less than 1.5 millimeters in diameter, the bearing axle coupling and extending from the actuator coupling through the inward-facing and outward-facing portions of the slot, and
- a bearing made from a third material and less than 3.0 millimeters in diameter, the bearing rotatably supported by the bearing axle in the outward-facing portion of the slot, the bearing being axially constrained by the lip of the slot;

wherein a first threshold galling stress between the first material and the second material is less than 10 kpsi, a second threshold galling stress between the first material and the third material is greater than 35 kpsi, and a third threshold galling stress between the second material and the third material is greater than 35 kpsi.

* * * * *